(12) United States Patent
Mori

(10) Patent No.: US 7,781,005 B2
(45) Date of Patent: Aug. 24, 2010

(54) SWEETENER COMPOSITION

(75) Inventor: Kenichi Mori, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 132 days.

(21) Appl. No.: 11/406,262

(22) Filed: Apr. 19, 2006

(65) Prior Publication Data

US 2006/0257550 A1  Nov. 16, 2006

Related U.S. Application Data

(63) Continuation-in-part of application No. 11/249,629, filed on Oct. 14, 2005, now abandoned.

(60) Provisional application No. 60/618,979, filed on Oct. 18, 2004.

(30) Foreign Application Priority Data

Oct. 15, 2004 (JP) .............................. 2004/302120

(51) Int. Cl.
*A23L 1/236* (2006.01)

(52) U.S. Cl. ........................ 426/548; 426/541; 426/590; 426/654

(58) Field of Classification Search ................... 426/72, 426/73, 541, 548, 590, 654
See application file for complete search history.

(56) References Cited

U.S. PATENT DOCUMENTS

| 5,994,559 | A | 11/1999 | Abushanab et al. |
| 2005/0004394 | A1 | 1/2005 | Kawahara et al. |
| 2005/0009153 | A1 | 1/2005 | Sugiyama et al. |
| 2005/0020508 | A1 | 1/2005 | Amino et al. |
| 2005/0106305 | A1 | 5/2005 | Abraham et al. |
| 2005/0272939 | A1 | 12/2005 | Amino et al. |
| 2006/0014819 | A1 | 1/2006 | Mori et al. |

FOREIGN PATENT DOCUMENTS

| WO | 03/045914 | 6/2003 |
| WO | 03/056026 | 7/2003 |
| WO | 03/059865 | 7/2003 |
| WO | 2004/053125 | 6/2004 |
| WO | 2004/067494 | 8/2004 |
| WO | 2005/014839 | 2/2005 |
| WO | 2005/016022 | 2/2005 |
| WO | 2005/020721 | 3/2005 |
| ZA | 87/4288 | 6/1987 |

OTHER PUBLICATIONS

R. Vleggaar et al, "Structure Elucidation of Monatin, a High-intensity Sweetener Isolated from the Plant *Schlerochiton ilicifolius*", *J. Chem. Soc. Perkin Trans*, 1, 1992, pp. 3095-3098.
C. W. Holzapfel et al, "A Simple Cycloaddition Approach to a Racemate of the Natural Sweetener Monatin", *Synthetic Communications*, 1994, vol. 24, No. 22, pp. 3197-3211.
K. Nakamura et al., "Total Synthesis of Monatin", *Organic Letters*, 2000, vol. 2, No. 19, pp. 2967-2970.

*Primary Examiner*—Leslie Wong
(74) *Attorney, Agent, or Firm*—Oblon, Spivak, McClelland, Maier & Neustadt, L.L.P.

(57) ABSTRACT

Storing monatin or a salt thereof in the presence of a radical scavenger and/or in a UV light-shielding container is effective for preventing the decomposition of monatin or a salt thereof by exposure to ultraviolet light, particularly under acidic conditions. Sweetener compositions which contain monatin or a salt thereof and a radical scavenger, a colorant, caffeine and the like are resistant to decomposition by UV light.

31 Claims, 5 Drawing Sheets

SWEETENER COMPOSITION

CROSS REFERENCES TO RELATED APPLICATIONS

This application is a continuation-in-part of U.S. patent application Ser. No. 11/249,629, filed on Oct. 14, 2005, now abandoned, and claims priority to U.S. Provisional Patent Application No. 60/618,979, filed on Oct. 18, 2004, and Japanese Patent Application No. 302120/2004, filed on Oct. 15, 2004, all of which are incorporated herein by reference in their entireties.

BACKGROUND OF THE INVENTION

1. Field of the Invention

The present invention relates to sweetener compositions comprising monatin or a salt thereof. More particularly, the present invention relates to a method for preserving monatin or a salt thereof.

2. Discussion of the Background

Monatin is a natural amino acid derivative isolated from the root bark of a native plant (Schlerochiton ilicifolius) of northern Transvaal of South Africa, and its structure has been reported by R. Vleggaar et al to be (2S,4S)-2-amino-4-carboxy-4-hydroxy-5-(3-indolyl)-pentanoic acid ((2S,4S)-4-hydroxy-4-(3-indolylmethyl)-glutamic acid) (R. Vleggaar et al., *J. Chem. Soc. Perkin Trans.*, pp. 3095-3098, (1992)). The synthesis of monatin is described in, for example, ZA 87/4288, ZA 88/4220, U.S. Pat. No. 5,994,559, WO03/045914, WO03/059865, WO03/056026, WO04/067494, WO04/053125, C. W. Holzapfel et al., *Synthetic Communications*, vol. 24(22), pp. 3197-3211 (1994), K. Nakamura et al., *Organic Letters*, vol. 2, pp. 2967-2970 (2000), and the like. Monatin is a superior sweetener which is 1400 times sweeter than sugar and contains no calories. It is stable to heat and expected to be applicable to various kinds of food.

SUMMARY OF THE INVENTION

The present inventor has first clarified at this time that monatin in the solution state tends to decompose when exposed to ultraviolet light, and that the tendency becomes particularly remarkable under acidic conditions (particularly at a pH of less than 5). As mentioned above, therefore, a means to use a superior sweetener, monatin, in a stable state irrespective of the condition it is placed in, becomes necessary.

Thus, the problem to be solved by the present invention solves the above-mentioned novel problem. Specifically, the problem of the present invention is to provide a method for preserving monatin or a salt thereof in a stable state even under ultraviolet light, and further, a sweetener composition, a beverage, a food, a pharmaceutical product and the like, which contain stable monatin or a salt thereof. In addition, provision of a preservation stabilizer for monatin or a salt thereof is also a problem of the present invention.

Accordingly, it is one object of the present invention to provide novel compositions which contain monatin or a salt thereof.

It is another object of the present invention to provide novel compositions which contain monatin or a salt thereof and which exhibit increased stability.

It is another object of the present invention to provide novel compositions which contain monatin or a salt thereof and which exhibit increased stability, even when exposed to ultraviolet light.

It is another object of the present invention to provide novel beverages, foods, pharmaceutical products, and the like, which contain stable monatin or a salt thereof.

These and other objects, which will become apparent during the following detailed description, have been achieved by the inventor's discovery that monatin and a salt thereof can be maintained in a stable state by maintaining monatin or a salt thereof in the co-presence of a radical scavenger.

Accordingly, the present invention provides the following:

(1) A sweetener composition, comprising monatin or a salt thereof and a radical scavenger.

(2) The composition of (1), wherein the radical scavenger is at least one member selected from the group consisting of ascorbic acid, ascorbate, ascorbic acid ester, erythorbic acid, erythorbic acid salt, erythorbic acid ester, uric acid, bilirubin, albumin, vitamin A, vitamin E, ubiquinol, carotenoid, histidine, tryptophan, 2,6-di-tert-butyl-4-methylphenol, 2-tert-butyl-4-hydroxyanisole, 3-tert-butyl-4-hydroxyanisole, propyl gallate, catechin, and mixtures thereof.

(3) The composition of (1), wherein the radical scavenger is at least one member selected from the group consisting of ascorbic acid, ascorbate, ascorbic acid ester, erythorbic acid, erythorbic acid salt, erythorbic acid ester, and mixtures thereof.

(4) The composition of (1), wherein the radical scavenger is ascorbic acid.

(5) The composition of any of (1)-(4), which is a liquid composition having a pH of not less than 2 and less than 7.

(6) The composition of any of (1)-(5), wherein the radical scavenger content is 1 to 10000 mass parts relative to 100 mass parts of monatin or a salt thereof.

(7) A beverage, a food, a mouth cavity composition, or a pharmaceutical product comprising a composition of any of (1)-(6).

(8) A beverage comprising a composition of any of (1)-(6).

(9) A preservation stabilizer for monatin or a salt thereof, which comprises a radical scavenger.

(10) A method of preserving monatin or a salt thereof, which comprises maintaining monatin or a salt thereof in the presence of a radical scavenger.

(11) A method of preserving a sweetener composition, a beverage, a food, a mouth cavity composition, or a pharmaceutical product, comprising monatin or a salt thereof, which method comprises maintaining monatin or a salt thereof in the presence of a radical scavenger.

(12) A method of preserving a beverage comprising monatin or a salt thereof, which method comprises maintaining monatin or a salt thereof in the presence of a radical scavenger.

(13) A method of preserving monatin or a salt thereof, which method comprises placing monatin or a salt thereof under a condition free of exposure to ultraviolet light.

(14) A method of preserving a sweetener composition, a beverage, a food, a mouth cavity composition, or a pharmaceutical product comprising monatin or a salt thereof, which method comprises placing monatin or a salt thereof under a condition free of exposure to ultraviolet light.

(15) A method of preserving a beverage comprising monatin or a salt thereof, which method comprises placing monatin or a salt thereof under a condition free of exposure to ultraviolet light.

(16) The method of (13)-(15), which comprises preservation in the presence of a radical scavenger.

(17) Monatin or a salt thereof, which is enclosed in a container shielding ultraviolet light.

(18) A sweetener composition, a beverage, a food, a mouth cavity composition, or a pharmaceutical product comprising monatin or a salt thereof, which is enclosed in a container shielding ultraviolet light.

(19) A beverage comprising monatin or a salt thereof, which is enclosed in a container shielding ultraviolet light.

(20) A sweetener composition, a beverage, a food, a mouth cavity composition, or a pharmaceutical product comprising monatin or a salt thereof and a radical scavenger, which is enclosed in a container shielding ultraviolet light.

(21) A beverage comprising monatin or a salt thereof and a radical scavenger, which is enclosed in a container shielding ultraviolet light.

(22) A sweetener composition comprising monatin or a salt thereof, and a colorant.

(23) The sweetener composition of (22), wherein the colorant shows local maximum photoabsorption in 300 nm-500 nm.

(24) A sweetener composition comprising monatin or a salt thereof, and caffeine.

According to the present invention, a sweetener composition, a food, a beverage, a mouth cavity composition, and a pharmaceutical product are provided, which contain monatin or a salt thereof, and which suppress decomposition of the monatin or salt thereof due to ultraviolet light, and provide a stable sweetness. According to the present invention, moreover, a preservation stabilizer for and a method of preserving monatin or a salt thereof are also provided.

DETAILED DESCRIPTION OF THE PREFERRED EMBODIMENTS

Figure 1:
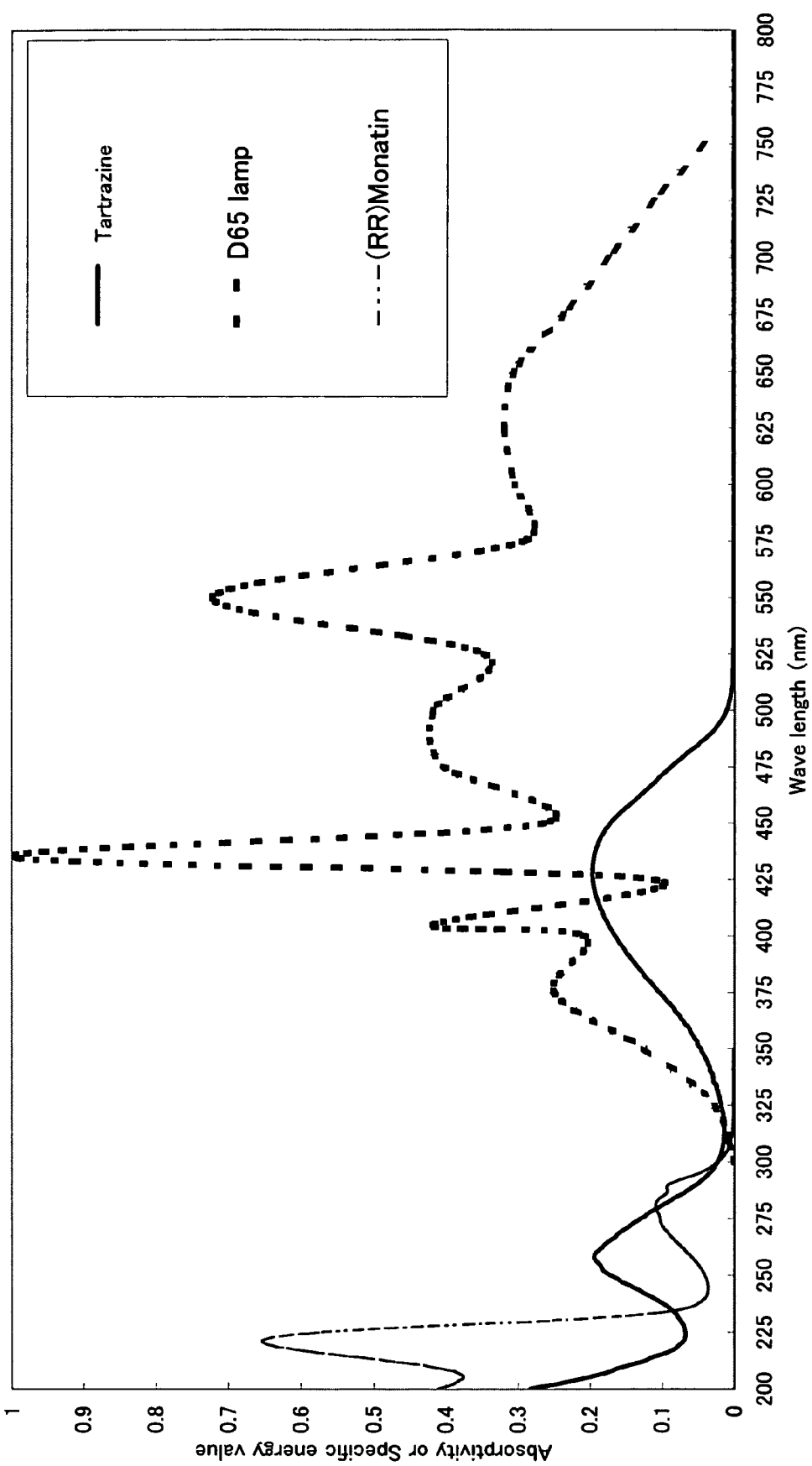
FIGS. 1-5 present photoabsorption spectra of (R,R) monatin and various colorants, which show energy distribution curves of D65 lamp.

The sweetener composition of the present invention contains monatin and a radical scavenger. Monatin is a compound represented by the formula (I):

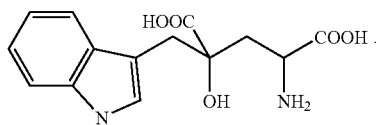

(I)

Monatin has an asymmetric moieties at the 2-position and the 4-position and includes the following 4 kinds of optical isomers.

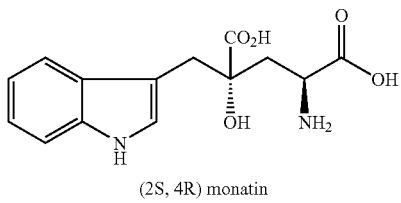

(2S, 4R) monatin

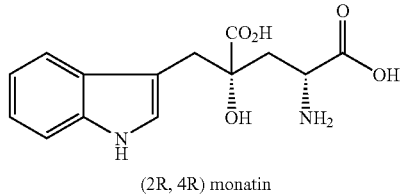

(2R, 4R) monatin

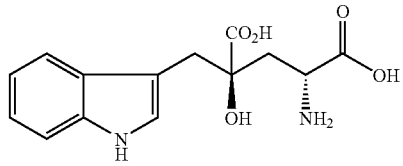

(2R, 4S) monatin

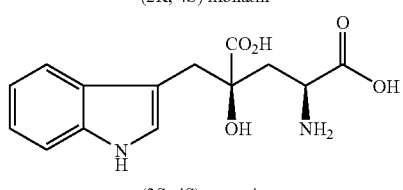

(2S, 4S) monatin

In the present invention, the stereoisomer is not particularly limited. Where necessary, (2R,4R)monatin, (2R,4S)monatin, (2S,4R)monatin, and (2S,4S)monatin, and any mixture of these can be used. Unless otherwise specified, in the present specification, simple monatin means one without limitation on stereoisomerism. Moreover, the monatin used in the present invention may be used as a salt with an alkali metal, such as sodium, potassium, and the like; an alkaline earth metal such as magnesium and the like; and the like. In this case, the potassium salt is preferable, and monopotassium salt is more preferable.

According to the finding of the present inventor, of the 4 kinds of optical isomers, (2S,4R)monatin and (2R,4S)monatin tend to be more easily decomposed by ultraviolet light than the other isomers. Monatin is a known substance, and its production method is also known. For example, it can be produced by a method described in ZA 87/4288, ZA 88/4220, U.S. Pat. No. 5,994,559, WO03/045914, WO03/059865, WO03/056026, WO04/067494, WO04/053125, C. W. Holzapfel et al., *Synthetic Communications*, vol. 24(22), pp. 3197-3211(1994), K. Nakamura et al., *Organic Letters*, vol. 2, pp. 2967-2970(2000), and the like.

The term radical scavenger as used in the present invention refers to a compound used to efficiently catch a radical (free group) produced during reaction and, for example, ascorbic acid, ascorbate, ascorbic acid ester, erythorbic acid (isoascorbic acid), erythorbic acid salt, erythorbic acid ester, uric acid, bilirubin, albumin, vitamin A, vitamin E, ubiquinol, carotenoid, histidine, tryptophan, 2,6-di-tert-butyl-4-methylphenol (BHT), 2-tert-butyl-4-hydroxyanisole, 3-tert-butyl-4-hydroxyanisole, propyl gallate, catechin, and the like can be mentioned. As the radical scavenger in the present invention, ascorbic acid, ascorbate, ascorbic acid ester, erythorbic acid, erythorbic acid salt, and erythorbic acid ester are preferable. As the salt of ascorbate or erythorbic acid salt, alkali metal salts (e.g., sodium salt, potassium salt, etc.) and the like can be mentioned. Particularly, a sodium salt is preferable. As the ascorbic acid ester or erythorbic acid ester, fatty acid esters (e.g., palmitic acid ester, stearic acid ester, and the like) are preferable. In the present invention, particularly preferable radical scavenger is ascorbic acid. As the ascorbic acid, L-ascorbic acid (vitamin C) is more preferable.

The content of the radical scavenger in the sweetener composition of the present invention is not particularly limited as long as the effect of the present invention is afforded, and the content is generally not less than 1 mass part, preferably not less than 5 mass parts, more preferably not less than 10 mass parts, relative to 100 mass parts of monatin or a salt thereof. The upper limit of the content is not particularly set and it is appropriately determined depending on the kind of radical scavenger to be used, and the kind of food on which a sweetener composition is used. A radical scavenger is generally used in an amount of not more than 10000 mass parts, preferably not more than 5000 mass parts, relative to 100 mass parts of monatin or a salt thereof.

The colorant to be used in the present invention is not particularly limited as long as it is generally used as a food dye and, for example, Bordeaux S, Tartrazine, Brilliant blue, Fast green, caramel and the like can be used. They may be used alone or in combination of two or more kinds thereof. Since photodegradation suppression efficiency is high, Bordeaux S, Tartrazine, Brilliant blue and Fast green are preferable, Tartrazine and Brilliant blue are more preferable, and Tartrazine is particularly preferable.

When a radical scavenger is added to a sweetener composition of the present invention comprising monatin and a colorant, the photodegradation reaction can be synergistically suppressed.

The content of the colorant in the sweetener composition of the present invention is not particularly limited as long as the effect of the present invention can be exhibited, and it is generally not less than 1 mass part, preferably not less than 5 mass parts, more preferably not less than 10 mass parts, per 100 mass parts of monatin or a salt thereof. The upper limit of the content of the colorant is not particularly limited, and appropriately determined depending on the kind of the radical scavenger to be used and the kind of the food for which a sweetener composition is used. It is generally not more than 10000 mass parts, preferably not more than 5000 mass parts, per 100 mass parts of monatin or a salt thereof.

Caffeine to be used in the present invention is not particularly limited.

The content of caffeine in the sweetener composition of the present invention is not particularly limited as long as the effect of the present invention can be exhibited, and it is generally not less than 1 mass part, preferably not less than 5 mass parts, more preferably not less than 10 mass parts, per 100 mass parts of monatin or a salt thereof. The upper limit of the content of caffeine is not particularly limited, and appropriately determined depending on the kind of the radical scavenger to be used and the kind of the food for which a sweetener composition is used. It is generally not more than 10000 mass parts, preferably not more than 5000 mass parts, per 100 mass parts of monatin or a salt thereof.

The sweetener composition of the present invention is preferably used as a sweetener, and may further contain other optional components such as a carrier, an extender, an excipient, an additive, a flavor, and the like as necessary. The sweetener composition of the present invention may contain other sweeteners such as saccharides (e.g., sucrose, invert sugar, isomerized sugar, glucose, fructose, lactose, maltose, trehalose, xylose. etc.); sugar alcohols (e.g., multitol, sorbitol, mannitol, erythritol, xylitol, lactitol, etc.); oligosaccharides; dietary fiber; aspartame; saccharin; acesulfame K; sucralose; and the like.

The form of the sweetener composition of the present invention is not particularly limited, and it is provided in various forms such as a freeze-dried product, a mixed and ground product, a liquid, an emulsion, and the like. The sweetener composition as a freeze-dried product or a mixed and ground product may be granulated, where necessary, by a method known to those of ordinary skill in the art such as dry granulation, wet granulation and the like, to give granules. For a liquid sweetener, water, alcohol, glycerol, propylene glycol, and the like can be used as a solvent to dissolve solute and, more preferably, water and alcohol can be used. For control of the specific gravity of each component, the amounts of the aforementioned composition and solvent to be added are adjusted according to methods known to those of ordinary skill in the art.

The sweetener composition of the present invention can be used for a wide variety of products including beverages, foods, pharmaceutical products, and the like. To be specific, various foods include powder juices, powder cocoas, instant coffee, chocolate, chewing gum, health foods, bread, cake, and the like, and various beverages such as coffee beverages, vegetable juice beverages, Japanese tea, Chinese tea, tea, milk beverages, soup beverages, carbonated beverages, sweet beverages, juice beverages, alcohol beverages, and the like. In addition, it can be used for various products that require a sweet taste such as toothpaste powders, pharmaceutical products and the like, and the like.

The present invention moreover provides a preservation stabilizer of monatin or a salt thereof. The preservation stabilizer is characterized in that it contains a radical scavenger. The radical scavenger is the same as those mentioned above. Using this preservation stabilizer, decomposition of monatin and a salt thereof can be suppressed even under ultraviolet light, and they can be used for a stable sweetener composition and the like. Where desired, any other components such as the above-mentioned extenders, excipients, additives, flavors, sweeteners other than monatin, and the like can be added as long as the object of the present invention can be achieved.

Generally, the preservation stabilizer of the present invention is so used as to make the mass ratio of monatin or a salt thereof and radical scavenger the same as the mass ratio of the composition explained above.

According to the findings of the present inventor, when monatin is present in a liquid state such as aqueous solution and the like, it tends to be decomposed by ultraviolet light, and a pronounced tendency is found in an acidic pH range (pH of 2 to 7). Decomposition is particularly remarkable when pH is not more than 6. In general, the pH of food is not less than 2, and the decomposition suppressive effect and preservation stabilization effect of monatin of the present invention become remarkable in sweetener compositions and food having a pH of not less than 2 and not more than 7, further not less than pH 2 and not more than 6, still further not less than pH 2 and not more than 5, and even further not less than pH 2 and not more than 4. Since decomposition of monatin due to ultraviolet light is observed when monatin is present in a liquid state such as aqueous solution and the like, the decomposition suppressive effect and preservation stabilization effect of the present invention is particularly remarkably exhibited in beverages containing monatin. In addition, the decomposition suppressive effect and preservation stabilization effect can be exhibited in food and pharmaceutical products containing monatin in a liquid state, food and pharmaceutical products containing monatin together with a solvent in which monatin is dissolved, and food and pharmaceutical products in which monatin is used or preserved in a liquid state. Furthermore, the decomposition suppressive effect and preservation stabilization effect can be exhibited in food and pharmaceutical products produced via a step comprising monatin in a liquid state during production thereof.

The term ultraviolet light refers to an electromagnetic wave having a shorter wavelength than visible light and a longer wavelength than X-ray, and the wavelength range thereof can be made to fall within the range of approximately 400 nm to 1 nm. Ultraviolet light is divided according to wavelength range into near ultraviolet light 400 to 300 nm, deep ultraviolet light 300 to 200 nm, and vacuum ultraviolet light 200 to 1 nm. Since absorption due to oxygen is seen in a wavelength range of not more than 195 nm, a spectroscope for this wavelength range requires a special design such as vacuum optical path and the like. Ozone in the upper atmosphere absorbs not more than about 290 nm of the sunlight. (Tokyo Kagaku Dozin Co., Ltd., Encyclopedia of Chemistry, 1 st ed. 4th printing, 1998). As is clear from the Examples to be mentioned later, light irradiation from a lamp with a UV absorption film hardly decomposes monatin, but irradiation of sunlight, D65 lamp and near ultraviolet lamp (all having a wavelength in the ultraviolet light region) decomposes monatin. It is clear therefrom that the decomposition of monatin is attributable to an electromagnetic wave having a wavelength in the ultraviolet light region (assumed to be mainly 290 to 400 nm wavelength).

According to the findings of the present inventor, when monatin is present in a liquid state, it is decomposed by ultraviolet light, namely, by the electromagnetic wave having a wavelength in the ultraviolet light region, and also decomposed by, for example, irradiation with sunlight. For example, when preserved in an ultraviolet shield, decomposition is hardly observed. Based on such finding, the present invention further provides a method of preserving monatin or a salt thereof, a method of preserving a sweetener composition containing monatin or a salt thereof, and a method of preserving a beverage, a food, a mouth cavity composition, or a pharmaceutical product containing monatin or a salt thereof.

A first preservation method includes maintaining monatin or a salt thereof in the presence of a radical scavenger. Generally, decomposition of monatin is observed when monatin or a salt thereof is present in a liquid state. However, since monatin may also become partially liquid and may be decomposed when it is present in a solid state (e.g., a powder, etc.) due to moisture absorption and the like, the preservation method of the present invention is useful for the retention of quality. Moreover, any other component such as the above-mentioned extenders, excipients, additives, flavors, sweeteners other than monatin, and the like may be co-existent. Generally, the preservation method of the present invention is so performed as to make the mass ratio of monatin or a salt thereof and radical scavenger similar to the mass ratio thereof in the composition explained earlier.

A second preservation method includes placing monatin or a salt thereof under the conditions free of exposure to ultraviolet light. To be specific, any state may be employed as long as monatin and a salt thereof are not exposed to ultraviolet light and, for example, placing them in a container made from an ultraviolet light shielding material, such as aluminum and the like, wrapping them with a film and the like, which shield ultraviolet light, placing them in a container colored with a colorant having an ultraviolet absorption ability, and the like can be mentioned. Therefore, the present invention also encompasses a means to prevent exposure of monatin or a salt thereof to ultraviolet light, for example, monatin or a salt thereof in a container, wherein monatin or a salt thereof is enclosed in a container that shields ultraviolet light, a sweetener composition, a beverage, a food, a mouth cavity composition, or a pharmaceutical product in a container, wherein monatin or a salt thereof is enclosed in a container that shields ultraviolet light, and the like. The ultraviolet absorption wavelength of the colorant that may be contained in the container is not particularly limited, and the lower limit of the absorption wavelength is preferably 200 nm, more preferably 250 nm, still more preferably 300 nm and particularly preferably 350 nm, and the upper limit of the absorption wavelength is preferably 700 nm, more preferably 650 nm, still more preferably 600 nm, still more preferably, and further more preferably 550 nm, and 500 nm is particularly more preferable because the effect can be afforded even with a smaller amount of the colorant.

A third preservation method includes placing monatin or a salt thereof in the coexistence with a colorant. Generally, decomposition of monatin is observed when monatin or a salt thereof is present in a liquid form. Monatin or a salt thereof in a solid form such as powder etc. may become partially liquid due to moisture absorption and the like and decomposed. From the aspects of quality maintenance, therefore, the preservation method of the present invention is useful. While the ultraviolet absorption wavelength of the colorant to be used is not particularly limited, from the aspects of achieving the effect with a smaller amount of the colorant, the lower limit of the absorption wavelength is preferably 200 nm, more preferably 250 nm, still more preferably 300 nm, and particularly preferably 350 nm, and the upper limit of the absorption wavelength is preferably 700 nm, more preferably 650 nm, still more preferably 600 nm, still further preferably 550 nm, and particularly preferably 500 nm. In this preservation method, moreover, optional components such as the above-mentioned extender, excipient, additive, flavoring, sweetener other than monatin and the like may be co-present besides monatin or a salt thereof and a colorant. The preservation method of the present invention is generally performed in such a manner that the mass ratio of monatin or a salt thereof and a colorant becomes the same as that of the composition explained above.

A fourth preservation method includes placing monatin or a salt thereof in coexistence with caffeine. Generally, decomposition of monatin is observed when monatin or a salt thereof is present in a liquid form. Monatin or a salt thereof in a solid form such as powder etc. may become partially liquid due to moisture absorption and the like and decomposed. From the aspects of quality maintenance, therefore, the preservation method of the present invention is useful. In this preservation method, moreover, optional components such as the above-mentioned extender, excipient, additive, flavoring, sweetener other than monatin and the like may be co-present besides monatin or a salt thereof and caffeine. The preservation method of the present invention is generally performed in such a manner that the mass ratio of monafin or a salt thereof and caffeine becomes the same as that of the composition explained above.

Even when monatin and the like are preserved under an ultraviolet light shield or monatin is enclosed in a container that shields ultraviolet light, it is still preferable to keep monatin in the presence of at least one of the components of a radical scavenger, a colorant or caffeine, because consumers and the like may use or re-preserve monatin and the like under an ultraviolet light condition.

Other features of the invention will become apparent in the course of the following descriptions of exemplary embodiments which are given for illustration of the invention and are not intended to be limiting thereof.

EXAMPLES

Various conditions, light irradiation conditions, and HPLC analysis conditions employed for the following Examples, Comparative Examples and Reference Example are as described below.

Various Conditions:
Monatin used: (2R,4R)monatin potassium salt, (2S,4S)monatin potassium salt, and (2S,4R)monatin potassium salt.
commercially available liquid: product name "Diet Coke" use-by date: Jul. 31, 2006/EEB
colorant: Bordeaux S (CI:16185), Tartrazine (CI:19140), Brilliant blue FCF (CI:42090), Fast green FCF (CI:42053), all manufactured by Wako Pure Chemical Industries, Ltd.
caramel (product name: Taiyo Caramel Z-80)
caffeine: manufactured by Wako Pure Chemical Industries, Ltd., reagent special grade
Preservation PET container: Toyo Seikan Kaisha, Ltd. PET bottle (type: STHH350SA, maximum content: 376 ml, height: 157 mm, maximum diameter: 60 mm, liquid filled: 370 ml).

Light Irradiation Conditions:
Illuminance:
2900-3100 LUX.
UV-A: 0.06 mW/cm$^2$.
UV-B: 0.006 mW/cm$^2$.

TABLE 1

| place | UV-A(360 nm) mW/cm$^2$ | UV-B(305 nm) | illuminance lux |
|---|---|---|---|
| outside 9:10 | 1.102 | 0.376 | 44,000 |
| outside 13:40 | 1.790 | 0.696 | 72,300 |
| outside 15:40 | 1.007 | 0.399 | 48,000 |
| near ultraviolet light lamp | 0.597 | 0.053 | 23 |
| D65 lamp | 0.06 | 0.006 | 2,900 |
| lamp with UV absorption film | 0.001 | 0.001 | 2,700 |

(ref.: illuminance about 700-1000 lux on indoor desk)
Temperature: 25° C. constant temperature room (forced circulation).
Apparatus:
Luminance meter: Tokyo Koden Ltd.
Digital luminance meter ANA-F11.
UV Radiometer: Topcon Corporation UV Radiometer UVR-3036/S.
(light receiver: UV-A (365 nm), UV-B (305 nm)).
Lamp: manufactured by Toshiba Corporation, tube diameter 32.5 mm, tube length 580 mm, 20 W (common).
D65 fluorescence lamp type: FL20S.D-EDL-D65.
Near ultraviolet light lamp type: FL20S.BLB.
Fluorescence lamp with UV absorption film type: FL20S.N-SDL-NU.
(the light emitted by D65 fluorescence lamp has similar spectrum as sunlight).

HPLC Analysis Conditions:
Instruments used:
Pump: LC-9A manufactured by Shimadzu Corporation.
Column oven: CTO-10A manufactured by Shimadzu Corporation.
Detector: SPD-10A manufactured by Shimadzu Corporation.
Autosampler: SIL-9A manufactured by Shimadzu Corporation.
Gradienter: LPG-1000 manufactured by Tokyo Rikakikai Co., Ltd.
Column: CAPCELL PAK C18 TYPE MG 5 μm 4.6 mm×250 mm manufactured by Shiseido Company, Limited.
Column temperature: 40° C.
Detention wavelength: 210 nm.
Mobile liquid composition:
Solution A 20 mm $KH_2PO_4$/acetonitrile=100/5.
Solution B acetonitrile alone.
Gradient pattern: (shown in Table 2).

TABLE 2

| Time (min) | Solution A (%) | Solution B (%) |
|---|---|---|
| 0 | 100 | 0 |
| 15 | 100 | 0 |
| 40 | 63 | 37 |
| 45 | 63 | 37 |

Injection volume: 10 min/μL.
Analysis cycle: 70 min/1 sample.

pH Measurement Conditions:
pH meter: type HM-30G, manufactured by DKK Toa Corporation.
pH standard solution: phosphate pH standard equimolal solution (JIS Z 8802) pH=7, manufactured by Junsei Chemical Co., Ltd.
Phthalate pH standard solution (JIS Z 8802) pH=4 manufactured by Junsei Chemical Co., Ltd.
Measurement method: two-point calibration by automatic temperature calibration was performed and pH of the model drink was measured.

Preservation of Monatin by Addition of Radical Scavenger.

Examples 1-10, Comparative Examples 1-5, and Reference Example 1

The pH of a beverage model solution, a (citric acid 2 g, sodium benzoate 0.045 g)/L solution, was adjusted with 8N sodium hydroxide. (2R, 4R)monatin potassium salt (25 mg) and various additives were dissolved in the adjusted beverage model solution (500 mL) and filled in PET containers. In Reference Example 1, L-Trp (25 mg) was added instead of monatin. In Example 10, monatin potassium salt (25 mg) and ascorbic acid (250 mg) were added to commercially available Coke (500 ml) instead of beverage model. The containers were left standing for about 165 hours in a constant temperature room controlled to room temperature 25° C. under a D65 fluorescence lamp adjusted to illuminance of about 3000 Lux. The solution was simultaneously filled in a 20 ml screw cap vial and left standing for the same time in the same constant temperature room under a light shield. These light exposure solutions and light shield solutions were subjected to HPLC analysis, and photodecomposition rates were calculated by the following formula:

The photodecomposition rate (%)=(1−(mass % concentration of monatin in light exposure solution/ mass % concentration of monatin in light shield solution))×100

The pH, monatin used, and additives used for each solution were as shown in Table 3. The results are shown in Table 3. From Table 3, it is clear that the decomposition of monatin was remarkably suppressed by the presence of a radical scavenger under light irradiation including ultraviolet light by D65 lamp.

As described in ZA 87/4288 and ZA 88/4220, monatin is known to be present as an equilibrium of a lactone form of the formula (II) and a lactam form of the formula (III) in an aqueous solution, and the content ratio of the lactone form and lactam form tends to increase with lower pHs of the solution.

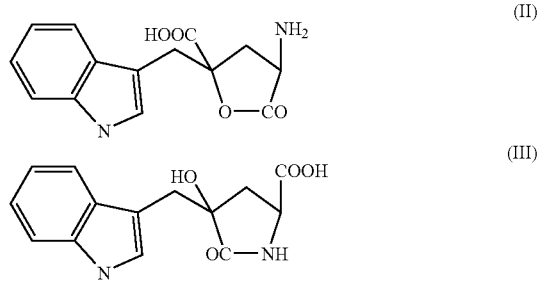

In the following Tables, the monatin residual ratio (%) is shown in the upper line, the lactone present ratio (%) is shown in the lower left line, and the lactam present ratio (%) is shown in the lower right line, all under light exposure and light shield.

The monatin residual ratio was calculated by the following formula:

The monatin residual ratio (%)=((monatin mass % concentration after light exposure or light shield preservation)/(monatin mass % concentration before light exposure or light shield preservation))×100

The presence rates of lactone and lactam were calculated by the following formula:

The lactone and lactam presence rates (%)=((HPLC peak area of lactam or lactone after light exposure or light shield preservation)/(HPLC peak area of monatin immediately after sample preparation))×100

The HPLC peak areas of lactone and lactam are not observed immediately after sample preparation.

Difference in Photodecomposition Rate of Monatin Due to pH Difference.

Comparative Examples 6-11

In the same manner as in Example 1, except that additives were not added, the photodecomposition rate of monatin was determined. The pH and monatin used for each solution are shown in Table 4. The results are shown in Table 4. From Table 4, it is clear that decomposition of monatin due to ultraviolet light tends to increase with lower pHs.

Decomposition Rate of Monatin with Ultraviolet Light Shield.

Examples 11-13

In the same manner as in Example 1, except that a fluorescence lamp with a UV absorption film (exposure time 73 hours) was used instead of a D65 lamp, the photodecomposition rate of monatin was determined. The pH, monatin, and additives used for each solution are shown in Table 5. The results are shown in Table 5. From Table 5, it is clear that decomposition of monatin was markedly suppressed when ultraviolet light was shielded.

Example 14 and Comparative Examples 12-13

In the same manner as in Example 1, except that sunlight (exposure time 14 hours) was used instead of a D65 lamp, the photodecomposition rate of monatin was determined. The pH, monatin, and additives used for each solution are shown in Table 6. The results are shown in Table 6. From Table 6, it is clear that the decomposition of monatin due to sunlight including ultraviolet light was markedly suppressed when a radical scavenger was present.

Example 15 and Comparative Examples 14-15

In the same manner as in Example 1, except that a near ultraviolet light lamp (exposure time 73 hours was used instead of a D65 lamp, the photodecomposition rate of monatin was determined. The pH, monatin, and additives used for each solution are shown in Table 7. The results are shown in Table 7. From Table 7, it is clear that the decomposition of monatin due to ultraviolet light was markedly suppressed when a radical scavenger was present.

pH Dependency of Photodecomposition Behavior of Trp and Monatin.

Reference Example 2

The pH dependency of the photodecomposition behavior of tryptophan (Trp) and monatin was examined.

For Trp, a solution having a concentration of 50 ppm was prepared (25° C.). The test solution was adjusted to a given pH with citrate buffer, and in the same manner as in Example 1, the photodecomposition rates of Trp and monatin were determined. The test conditions and results are shown in Table 8. From Table 8, it is clear that Trp tends to show photodecomposition in a neutral region rather than in an acidic region, and the photodecomposition behavior of monatin having an indole structure as does Trp is strikingly different from that of Trp, as evidenced by the tendency toward photodecomposition in an acidic region rather than in a neutral region, and the like. Therefore, the photodecomposition property of monatin cannot be predicted at all from the finding in the photodecomposition property of Trp.

Furthermore, it was surprisingly found that addition of ascorbic acid to monatin afforded an effect comparable to shading over a wide pH range.

Preservation of Monatin by Addition of Colorant

Examples 16-20

The pH of a beverage model [solution of (citric acid 2 g, sodium benzoate 0.045 g)/L] was adjusted with 8N sodium hydroxide. (2R,4R) monatin potassium salt (25 mg) and predetermined amounts of various colorants were dissolved in the adjusted beverage model solution (500 mL) and filled in a PET container. The results are shown in Table 9. It is clear from Table 9 that the decomposition of monatin was markedly suppressed under irradiation of light including UV light from a D65 lamp, by the copresence of the colorants.

Absorbance of Monatin and Various Colorants

Experimental Example

The following sample solution was prepared and the photoabsorption spectra were measured using a measurement apparatus. The results are shown in FIG. 1.

<apparatus> Varian UV-Visible Spectrophotometer: Cary 50

<measurement conditions> room temperature, quartz cell, wavelength 1 cm

<sample 1> (2R,4R)monatin potassium salt was dissolved in pure water and, after equivalent neutralization with diluted hydrochloric acid, diluted to 6.7 ppm as a free form of monatin.

<sample 2> Tartrazine (CI:19140) was dissolved in pure water and diluted to 5 ppm.

<spectral distribution of D65 lamp> Toshiba Lamp General Catalog 2004, p. 118

Figure 2:
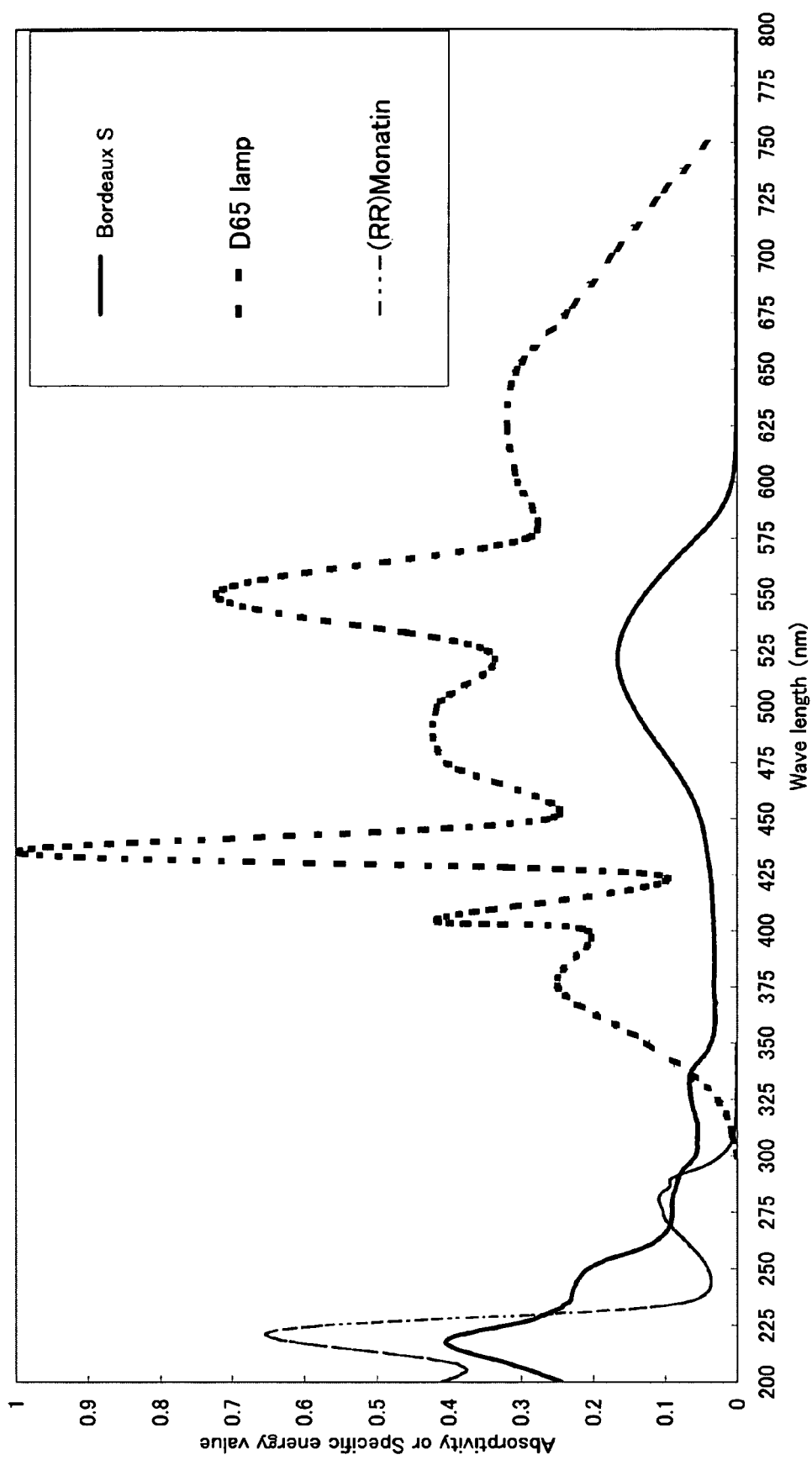
Figure 3:
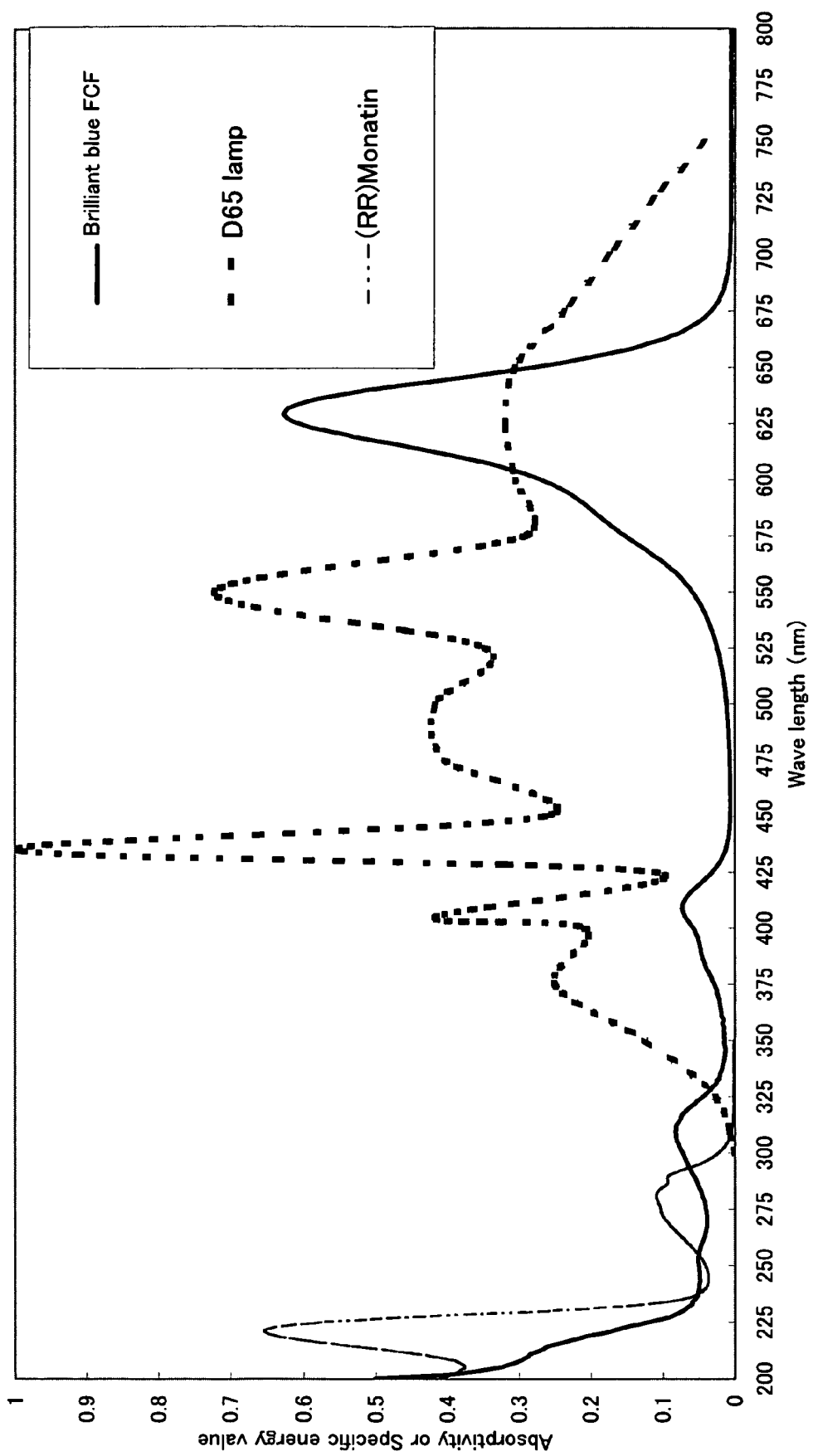
Figure 4:
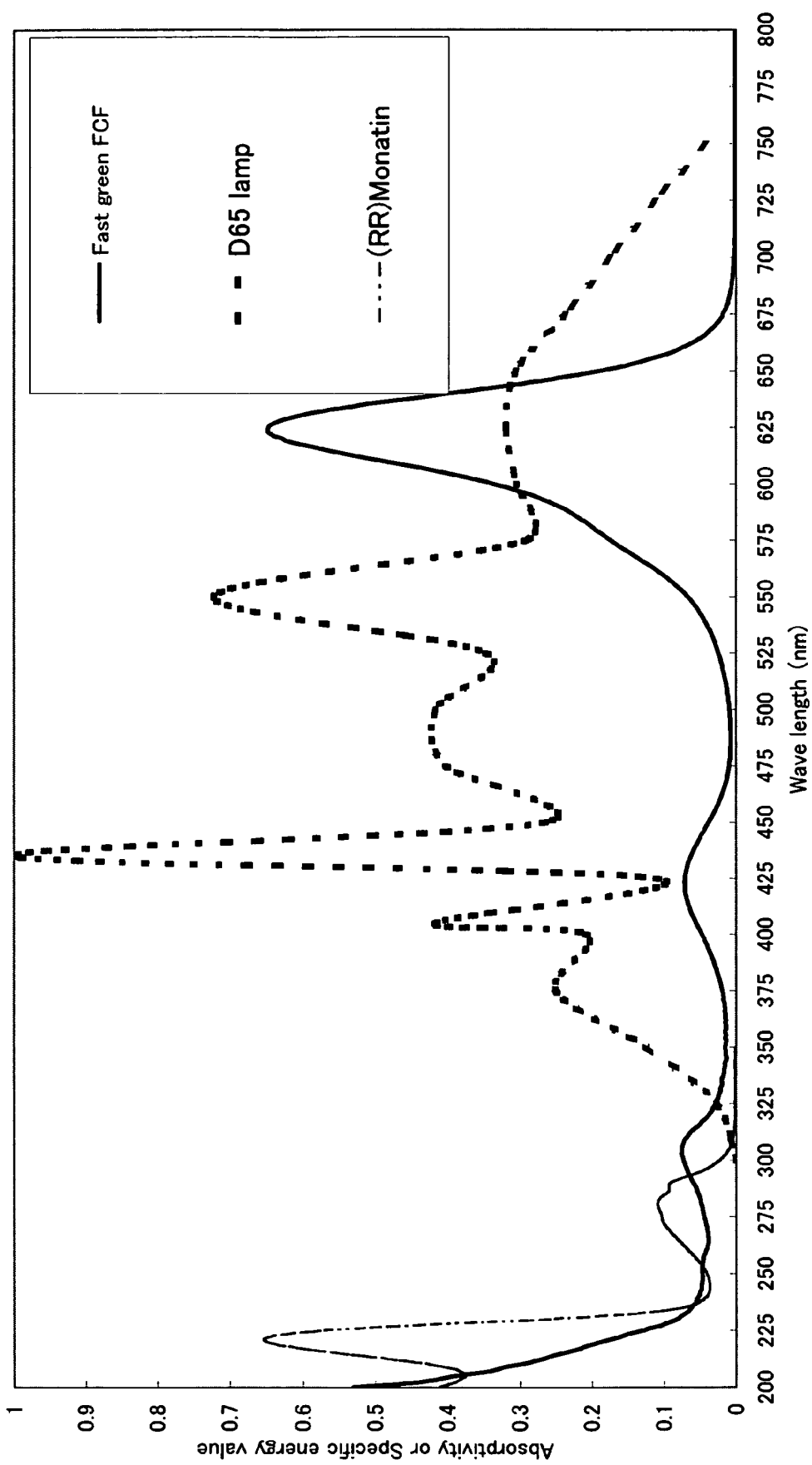
Figure 5:
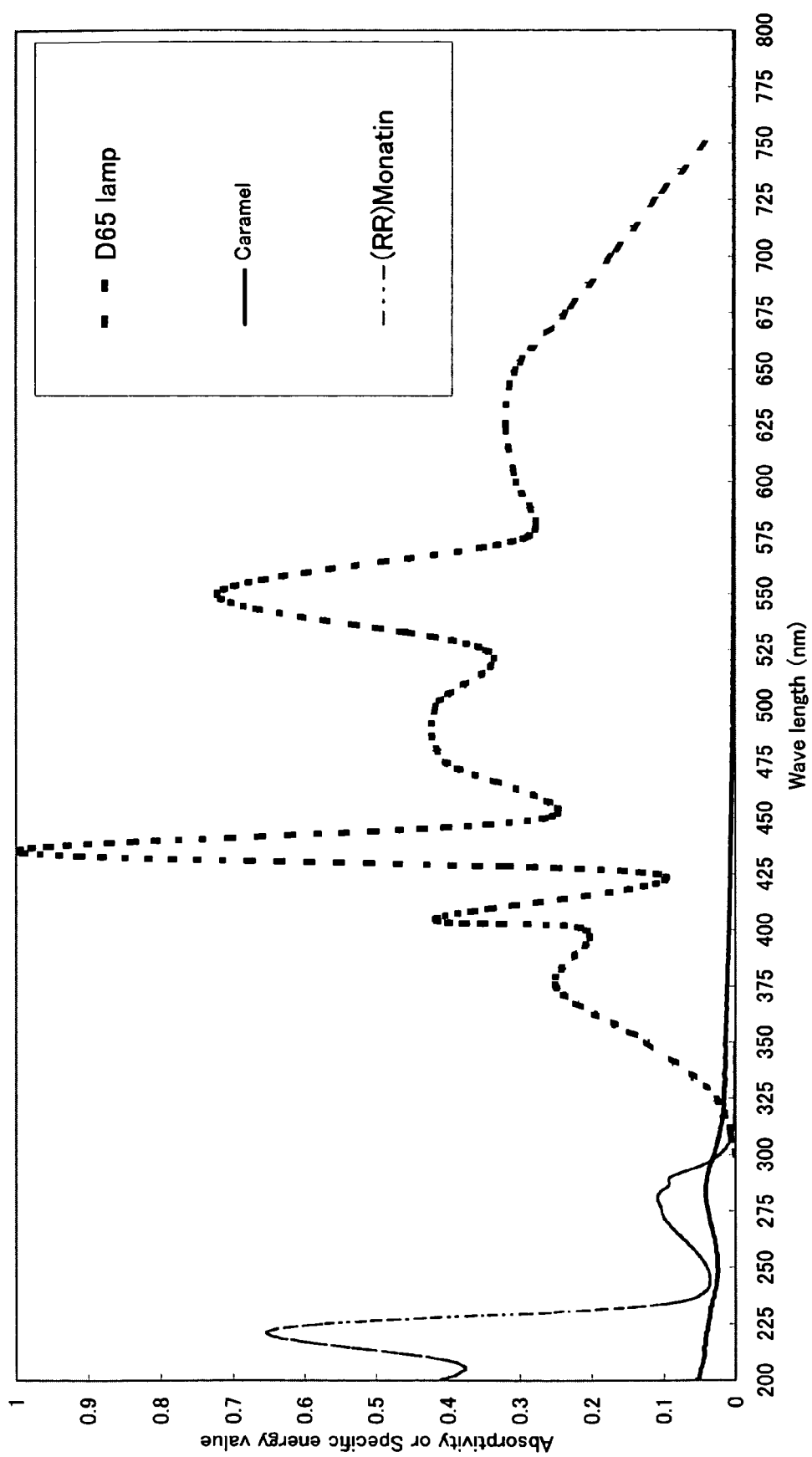

Furthermore, using Bordeaux S (FIG. 2), brilliant blue FCF (FIG. 3), Fast green (FIG. 4) and caramel (FIG. 5) as <sample 2> instead of Tartrazine, photoabsorption spectra were obtained in the same manner as above.

Preservation of Monatin by Addition of Caffeine

Example 21

The pH of a beverage model [solution of (citric acid 2 g, sodium benzoate 0.045 g)/L] was adjusted with 8N sodium hydroxide. (2R,4R) monatin potassium salt (25 mg) and caffeine (250 mg) were dissolved in the adjusted beverage model solution (500 mL) and filled in a PET container. The results are shown in Table 10. It is clear from Table 10 that the decomposition of monatin was markedly suppressed under irradiation of light including UV light from a D65 lamp, by the copresence of caffeine.

TABLE 3

| | | | | | | |
|---|---|---|---|---|---|---|
| | | | Light source D65 lamp illuminance 3000 lux exposure time 165 hr | | | |
| | pH | monatin | additive | light exposure | light shielding | photodecomposition rate |
| Ex. 1 | 3.1 | (2R, 4R) | ascorbic acid 25 mg (50 ppm) | 71.3% (25.7%, 1.2%) | 64.0% (23.2%, 1.7%) | −11.5% |
| Ex. 2 | 3.1 | (2R, 4R) | ascorbic acid 0.25 mg (0.5 ppm) | 54.6% (16.6%, 0.1%) | 76.9% (20.8%, 1.0%) | 29.1% |
| Ex. 3 | 3.1 | (2R, 4R) | ascorbic acid 2.5 mg (5 ppm) | 75.0% (21.2%, 0.9%) | 74.4% (25.1%, 1.8%) | −0.9% |
| Ex. 4 | 3.1 | (2R, 4R) | ascorbic acid 250 mg (500 ppm) | 72.8% (26.2%, 1.7%) | 68.8% (25.1%, 1.8%) | −5.7% |
| Ex. 5 | 3.1 | (2R, 4R) | BHT 25 mg (50 ppm) | 67.4% (19.4%, 0.9%) | 76.6% (21.3%, 1.0%) | 12.0% |
| Ex. 6 | 3.1 | (2R, 4R) | catechin 25 mg (50 ppm) | 74.9% (21.2%, 0.5%) | 77.3% (21.6%, 1.0%) | 3.1% |
| Ex. 7 | 3.1 | (2S, 4S) | ascorbic acid 25 mg (50 ppm) | 75.5% (12.2%, 0.7%) | 73.1% (19.9%, 0.9%) | −3.3% |
| Ex. 8 | 3.1 | (2S, 4R) | ascorbic acid 25 mg (50 ppm) | 63.3% (13.2%, 1.4%) | 62.6% (36.3%, 1.6%) | −1.1% |
| Ex. 9 | 3.1 | (2S, 4S) (2R, 4R) | ascorbic acid 25 mg (50 ppm) | 75.3% (13.2%, 1.4%) | 72.3% (20.9%, 0.9%) | −4.1% |
| Ex. 10* | | (2R, 4R) | ascorbic acid 250 mg (500 ppm) | 73.1% (24.1%, —) | 78.2% (24.7%, —) | 6.5% |
| Com. Ex. 1 | 3.1 | (2R, 4R) | none | 42.4% (12.5%, 0.6%) | 77.3% (21.6%, 0.9%) | 45.1% |
| Com. Ex. 2 | 3.1 | (2S, 4S) | none | 41.0% (12.2%, 0.7%) | 77.9% (21.1%, 1.1%) | 47.4% |
| Com. Ex. 3 | 3.1 | (2S, 4R) | none | 7.9% (5.5%, 0.0%) | 63.6% (39.5%, 1.7%) | 87.6% |
| Com. Ex. 4 | 3.1 | (2S, 4S) (2R, 4R) | none | 46.6% (14.1%, 0.8%) | 80.8% (22.2%, 0.1%) | 42.3% |
| Com. Ex. 5 | 3.1 | (2R, 4R) | trehalose 25 mg | 42.1% (12.3%, 0.8%) | 77.0% (21.3%, 1.0%) | 45.3% |
| Ref. Ex. 1 | 3.1 | L-Trp | none | 94.0% | 100.0% | 6.0% |

*In Ex. 10, commercially available Coke was used instead of the beverage model.

TABLE 4

Light source D65 lamp illuminance 3000 lux exposure time 165 hr

|  | pH monatin | additive | light exposure | light shielding | photodecomposition rate |
|---|---|---|---|---|---|
| Com. Ex. 6 | 2.8 (2R, 4R) | none | 36.8% (13.0%, 0.9%) | 77.4% (25.5%, 13%) | 52.5% |
| Com. Ex. 7 | 3.5 (2R, 4R) | none | 63.4% (11.5%, 0.5%) | 87.6% (14.7%, 0.5%) | 27.6% |
| Com. Ex. 8 | 4.0 (2R, 4R) | none | 79.8% (6.5%, 0.0%) | 94.8% (7.1%, 0.0%) | 15.9% |
| Com. Ex. 9 | 4.5 (2R, 4R) | none | 89.8% (2.6%, 0.0%) | 100.0% (2.7%, 0.0%) | 10.2% |
| Com. Ex. 10 | 5.5 (2R, 4R) | none | 96.9% (0.0%, 0.0%) | 101.8% (0.0%, 0.0%) | 4.8% |
| Com. Ex. 11 | 6.5 (2R, 4R) | none | 97.3% (0.0%, 0.0%) | 101.7% (0.0%, 0.0%) | 4.3% |

TABLE 5

Light source fluorescence lamp with UV absorption film 73 hr

|  | pH monatin | additive | light exposure | light shielding | photodecomposition rate |
|---|---|---|---|---|---|
| Ex. 11 | 3.1 (2R, 4R) | ascorbic acid 25 mg (50 ppm) | 76.7% (21.1%, 0.6%) | 74.2% (20.0%, 0.5%) | −3.4% |
| Ex. 12 | 3.1 (2R, 4R) | $K_2SO_3$ 25 mg (50 ppm) | 74.4% (20.0%, 0.5%) | 76.0% (20.0%, 0.5%) | 2.1% |
| Ex. 13 | 3.1 (2R, 4R) | none | 75.2% (20.9%, 1.4%) | 76.8% (20.9%, 0.5%) | 2.1% |

TABLE 6

Light source: sunlight, 14 hr

|  | pH monatin | additive | light exposure | light shielding | photodecomposition rate |
|---|---|---|---|---|---|
| Ex. 14 | 3.1 (2R, 4R) | ascorbic acid 25 mg (50 ppm) | 77.3% (22.2%, 0.6%) | 74.2% (20.1%, 0.5%) | −4.2% |
| Com. Ex. 12 | 3.1 (2R, 4R) | $K_2SO_3$ 25 mg (50 ppm) | 2.2% (0.7%, 0.0%) | 76.0% (20.0%, 0.5%) | 97.2% |
| Com. Ex. 13 | 3.1 (2R, 4R) | none | 41.9% (13.3%, 0.9%) | 76.8% (20.9%, 0.5%) | 45.4% |

TABLE 7

Light source: near ultraviolet light lamp; 73 hr

|  | pH monatin | additive | light exposure | light shielding | photodecomposition rate |
|---|---|---|---|---|---|
| Ex. 15 | 3.1 (2R, 4R) | ascorbic acid 25 mg (50 ppm) | 76.2% (21.0%, 0.6%) | 74.2% (20.1%, 0.5%) | −2.7% |
| Com. Ex. 14 | 3.1 (2R, 4R) | $K_2SO_3$ 25 mg (50 ppm) | 3.9% (0.8%, 0.0%) | 76.0% (20.0%, 0.5%) | 94.8% |
| Com. Ex. 15 | 3.1 (2R, 4R) | none | 16.3% (6.3%, 1.4%) | 76.8% (20.9%, 0.5%) | 78.8% |

TABLE 8

Light source: D65 lamp illuminance 3000 lux, exposure time 165 hr photodecomposition rate

| pH | Trp (50 ppm) | monatin (50 ppm) | monatin (50 ppm) + ascorbic acid (50 ppm) |
|---|---|---|---|
| 2.8 | 7.3% | 52.5% | not measured |
| 3.1 | 6.0% | 45.1% | −2% |
| 3.5 | 6.2% | 27.6% | not measured |
| 4 | 5.5% | 15.9% | not measured |
| 4.5 | 5.4% | 10.2% | −1% |
| 5.5 | 12.5% | 4.8% | not measured |
| 6.5 | 55.1% | 4.3% | 0% |

TABLE 9

Light source: D65 lamp illuminance 3000 lux, exposure time 166 hr

|  | pH | colorant | amount added | light exposure | light shielding | photodecomposition rate |
|---|---|---|---|---|---|---|
| Ex. 16 | 3.1 | Bordeaux S | 50 ppm | 67.1% | 76.1% | 11.9% |
| Ex. 17 | 3.1 | Tartrazine | 50 ppm | 77.0% | 76.7% | −0.36% |
| Ex. 18 | 3.1 | Brilliant blue FCF | 50 ppm | 74.4% | 75.2% | 1.0% |
| Ex. 19 | 3.1 | Fast green FCF | 50 ppm | 74.5% | 77.6% | 4.6% |
| Ex. 20 | 3.1 | caramel | 3750 ppm | 48.5% | 66.7% | 27.3% |

TABLE 10

Light source: D65 lamp illuminance 3000 lux, exposure time 498 hr

|  | pH | amount added | light exposure | light shielding | photodecomposition rate |
|---|---|---|---|---|---|
| Ex. 21 | 5.0 | 500 ppm | 84.6% | 101% | 16.4% |
| Com. Ex. 16 | 5.0 | 0 ppm | 75.5% | 102% | 25.7% |

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of preserving monatin or a salt thereof, said method comprising maintaining monatin or a salt thereof in a composition which consists essentially of monatin, a radical scavenger, and optionally one or more components selected from the group consisting of water, a buffer, sodium benzoate, caffeine, a colorant, a vitamin, an alcohol, glycerol, propylene glycol, and another sweetener.

2. The method of claim 1, wherein said composition is a sweetener composition, a beverage, a food, a mouth cavity composition, or a pharmaceutical product.

3. The method of claim 1, wherein said composition is a beverage.

4. The method of claim 1, wherein said radical scavenger is at least one member selected from the group consisting of ascorbic acid, ascorbate, an ascorbic acid ester, erythorbic acid, erythorbic acid salt, an erythorbic acid ester, uric acid, bilirubin, albumin, vitamin A, vitamin E, ubiquinol, carotenoid, histidine, tryptophan, 2,6-di-tert-butyl-4-methylphenol, 2-tert-butyl-4-hydroxyanisole, 3-tert-butyl-4-hydroxyanisole, propyl gallate, catechin, and mixtures thereof.

5. The method of claim 1, wherein said radical scavenger is at least one member selected from the group consisting of ascorbic acid, ascorbate, an ascorbic acid ester, erythorbic acid, erythorbic acid salt, an erythorbic acid ester, and mixtures thereof.

6. The method of claim 1, wherein said radical scavenger is ascorbic acid.

7. The method of claim 1, wherein said composition is a liquid composition having a pH of not less than 2 and less than 7.

8. The method of claim 1, wherein said radical scavenger is present in an amount of 1 to 10000 mass parts relative to 100 mass parts of said monatin or a salt thereof.

9. The method of claim 1, further comprising placing said composition under a condition free of exposure to ultraviolet light.

10. The method of claim 1, wherein said composition contains a colorant.

11. The method of claim 10, wherein said colorant shows local maximum photoabsorption in 300 nm to 500 nm.

12. The method of claim 1, wherein said composition contains caffeine.

13. A method of preserving monatin or a salt thereof, said method comprising maintaining monatin or a salt thereof in a composition which consists of monatin, a radical scavenger, and optionally one or more components selected from the group consisting of water, a buffer, sodium benzoate, caffeine, a colorant, a vitamin, an alcohol, glycerol, propylene glycol, and another sweetener.

14. The method of claim 13, wherein said composition is a sweetener composition, a beverage, a food, a mouth cavity composition, or a pharmaceutical product.

15. The method of claim 13, wherein said composition is a beverage.

16. The method of claim 13, wherein said composition contains a colorant.

17. The method of claim 16, wherein said colorant shows local maximum photoabsorption in 300 nm to 500 nm.

18. The method of claim 13, wherein said composition contains caffeine.

19. The method of claim 13, wherein said radical scavenger is at least one member selected from the group consisting of ascorbic acid, ascorbate, an ascorbic acid ester, erythorbic acid, erythorbic acid salt, an erythorbic acid ester, uric acid, bilirubin, albumin, vitamin A, vitamin E, ubiquinol, carotenoid, histidine, tryptophan, 2,6-di-tert-butyl-4-methylphenol, 2-tert-butyl-4-hydroxyanisole, 3-tert-butyl-4-hydroxyanisole, propyl gallate, catechin, and mixtures thereof.

20. The method of claim 13, wherein said radical scavenger is at least one member selected from the group consisting of ascorbic acid, ascorbate, an ascorbic acid ester, erythorbic acid, erythorbic acid salt, an erythorbic acid ester, and mixtures thereof.

21. The method of claim 13, wherein said radical scavenger is ascorbic acid.

22. The method of claim 13, which wherein said composition is a liquid composition having a pH of not less than 2 and less than 7.

23. The method of claim 13, wherein said radical scavenger is present in an amount of 1 to 10000 mass parts relative to 100 mass parts of said monatin or a salt thereof.

24. The method of claim 13, further comprising placing said monatin or a salt thereof under a condition free of exposure to ultraviolet light.

25. A method of preserving (2R,4R) monatin or a salt thereof, comprising:
    maintaining the (2R,4R) monatin or salt thereof in a liquid composition comprising a radical scavenger;
    wherein:
    the liquid composition has a pH of not less than 2 and less than 5;
    the radical scavenger comprises at least one member selected from the group consisting of ascorbic acid, ascorbate and an ascorbic acid ester; and
    the radical scavenger is present in an amount of at least 10 parts by mass relative to 100 parts by mass of the (2R, 4R) monatin or salt thereof.

26. The method of claim 25, wherein:
    the liquid composition comprises a colorant; and
    the colorant comprises at least one member selected from the group consisting of tartrazine, brilliant blue FCF and fast green FCF.

27. The method of claim 25, wherein the (2R,4R) monatin or salt thereof is maintained in a condition free from exposure to ultraviolet light.

28. The method of claim 25, wherein the liquid composition is placed under exposure to ultraviolet light.

29. The method of claim 25, wherein the radical scavenger is present in an amount of from 10 to 10,000 parts by mass relative to 100 parts by mass of the (2R,4R) monatin or salt thereof.

30. The method of claim 25, wherein the (2R,4R) monatin or salt thereof is provided in a sweetener composition, a beverage, a food, a mouth cavity composition or a pharmaceutical product.

31. The method of claim 30, wherein the sweetener composition, beverage, food, mouth cavity composition or pharmaceutical product further comprises caffeine.

* * * * *